United States Patent

Hakamata

[11] Patent Number: 5,772,593
[45] Date of Patent: Jun. 30, 1998

[54] SURGICAL OPERATION AIDING SYSTEM

[75] Inventor: Kazuo Hakamata, Kanagawa-ken, Japan

[73] Assignee: Fuji Photo Film Co., Ltd., Kanagawa, Japan

[21] Appl. No.: 678,265

[22] Filed: Jul. 11, 1996

[51] Int. Cl.$^6$ .................................................... A61B 6/00
[52] U.S. Cl. .............................. 600/407; 606/130; 348/77
[58] Field of Search ............................. 128/653.1, 653.2; 606/130; 250/330, 370.08, 458.1; 348/77; 600/407, 410

[56] References Cited

U.S. PATENT DOCUMENTS 5,526,812  6/1996  Dumoulin et al. .................... 128/653.1

FOREIGN PATENT DOCUMENTS

| 63-9464 | 2/1988 | Japan | A61B 110/00 |
| 1136630 | 5/1989 | Japan | A61B 5/00 |
| 759783 | 3/1995 | Japan | A61B 10/00 |

*Primary Examiner*—Marvin M. Lateef
*Assistant Examiner*—Eleni Mantis Mercader
*Attorney, Agent, or Firm*—Sughrue, Mion, Zinn, Macpeak & Seas, PLLC

[57] ABSTRACT

A surgical operation aiding system comprises an apparatus for obtaining an image signal representing an image of a sick portion of a living body, which is to undergo a surgical operation, and an image displaying apparatus for reproducing the image of the sick portion from the image signal and displaying the reproduced image on the actual sick portion of the living body. The magnification and/or the orientation of the displayed image is adjusted such that the position of the actual sick portion of the living body and the position of the pattern of the sick portion in the displayed image may match with each other.

3 Claims, 2 Drawing Sheets

SURGICAL OPERATION AIDING SYSTEM

BACKGROUND OF THE INVENTION

1. Field of the Invention

This invention relates to a surgical operation aiding system for helping a surgical operator to confirm the position of the diseased part contained in a sick portion of a living body when he conducts a surgical operation on the living body.

2. Description of the Prior Art

Heretofore, extensive research has been carried out on technique, which is generally referred to as the photodynamic diagnosis (PDD). With the PDD technique, a tumor part of a living body is caused to absorb a light-sensitive substance, which has an affinity for tumors and is capable of producing fluorescence when it is stimulated by light. Stimulating rays, which have wavelengths falling within the stimulation wavelength range for the light-sensitive substance, are then irradiated to the tumor part, and the light-sensitive substance having been absorbed by the tumor part is thereby caused to produce the fluorescence. An image formed with the fluorescence is displayed and used in making a diagnosis.

Fluorescent image sensing apparatuses for carrying out the PDD technique have been proposed in, for example, Japanese Patent Publication No. 63(1988)-9464 and Japanese Unexamined Patent Publication Nos. 1(1989)-136630 and 7(1995)-59783. Basically, the fluorescent image sensing apparatuses of these types comprise a stimulating ray irradiating means for irradiating the stimulating rays, which have wavelengths falling within the stimulation wavelength range for the light-sensitive substance, to the living body, and a means for detecting the fluorescence produced by the light-sensitive substance and converting the fluorescent image of the living body into an electric image signal. In many cases, the fluorescent image sensing apparatuses are incorporated in endoscopes, which are to be inserted into the living bodies, microscopes for surgical operations, or the like.

As described above, the light-sensitive substance has the affinity for tumors. Therefore, when the image of the sick portion having been detected by the aforesaid fluorescent image sensing apparatuses is displayed on an image displaying means, the infiltration range of the tumor is displayed as the fluorescent image. Accordingly, the surgical operator can ascertain the infiltration range of the tumor by making reference to the displayed image and can thereby determine an appropriate region, which is to be cut off from the sick portion of the living body.

In general, the fluorescence produced by the light-sensitive substance described above is very weak. Therefore, when the fluorescent image is to be detected by the fluorescent image sensing apparatus, which is incorporated in the microscope for surgical operations, or the like, it is necessary for the lightness in the operating room to be reduced markedly. If the operating room is thus set to be dark, the actual sick portion will become difficult to view. Therefore, even if the tumor part is displayed as the fluorescent image on the image displaying means in the manner described above, it will be difficult to make a judgment as to which position in the actual sick portion the position of the tumor part being displayed as the fluorescent image corresponds to.

Also, the fluorescent image displayed on the image displaying means gives a feeling markedly different from the feeling of the actual sick portion, which is given when the actual sick portion is viewed with the human eyes. Therefore, particularly in cases where the surgical operator is not skilled, even if the operating room is well lighted, the problems will often occur in that it cannot be found easily which position in the fluorescent image corresponds to which position in the actual sick portion, and in that it cannot be discriminated which position in the actual sick portion the position of the tumor part being displayed in the fluorescent image corresponds to.

SUMMARY OF THE INVENTION

The primary object of the present invention is to provide a surgical operation aiding system, which is capable of helping a surgical operator to confirm the position of the diseased part contained in a sick portion of a living body when he conducts a surgical operation on the living body.

The present invention provides a surgical operation aiding system, comprising:

i) an apparatus for obtaining an image signal representing an image of a sick portion of a living body, which is to undergo a surgical operation, ii) an image displaying apparatus for reproducing the image of the sick portion from the image signal and displaying the reproduced image on the actual sick portion of the living body, and iii) a position matching means for adjusting the magnification and/or the orientation of the displayed image such that the position of the actual sick portion of the living body and the position of the pattern of the sick portion in the displayed image may match with each other.

With the surgical operation aiding system in accordance with the present invention, the image of the sick portion of the living body is displayed on the actual sick portion of the living body such that the position of the actual sick portion of the living body and the position of the pattern of the sick portion in the displayed image may match with each other. Therefore, in cases where the pattern of the diseased part is being indicated in the displayed image, the pattern of the diseased part is displayed at the position overlapping upon the actual diseased part in the sick portion of the living body. Accordingly, the surgical operator can easily and accurately confirm the position, at which the diseased part is located.

DESCRIPTION OF THE PREFERRED EMBODIMENTS

The present invention will hereinbelow be described in further detail with reference to the accompanying drawings.

Figure 1:
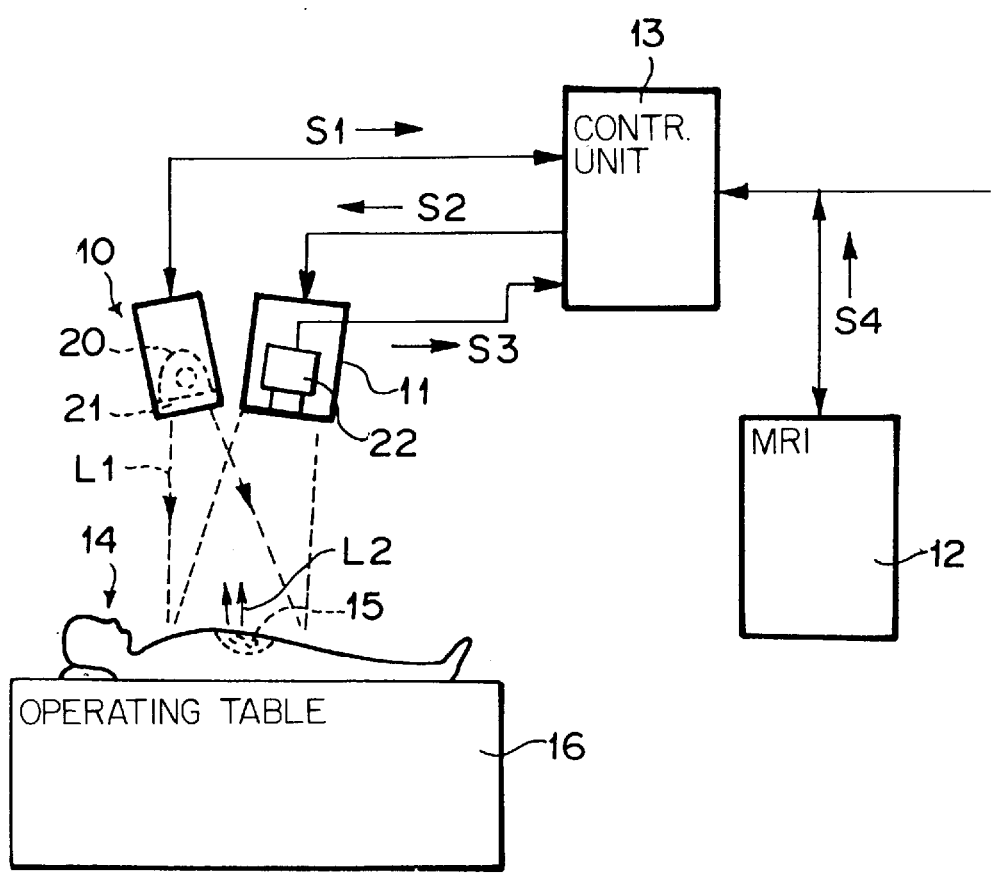
FIG. 1 is a schematic view showing an embodiment of the surgical operation aiding system in accordance with the present invention.

FIG. 1 is a schematic view showing an embodiment of the surgical operation aiding system in accordance with the present invention. The surgical operation aiding system comprises a fluorescent image sensing apparatus 10, an image projecting apparatus 11, a magnetic resonance imaging (MRI) apparatus 12, and a control unit 13, which is connected to the apparatuses 10, 11, and 12.

Figure 2:
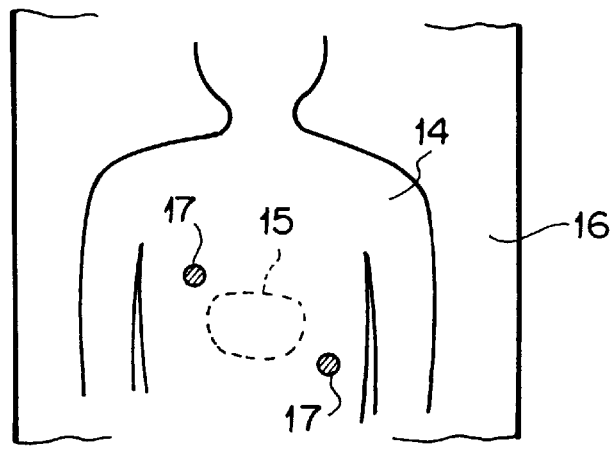
FIG. 2 is a plan view showing a patient, whose fluorescent image is detected.

A sick portion 15 of a patient 14, who is to undergo a surgical operation, is caused to absorb a light-sensitive substance, which has an affinity for tumors and is capable of producing the fluorescence when it is stimulated by light. As the light-sensitive substance, a porphyrin type of substance, or the like, may be employed. As illustrated in FIG. 2, the patient 14 lies at a predetermined position on an operating table 16. By way of example, two fluorescent markers 17, 17 for position matching are secured to predetermined positions on the patient 14.

The fluorescent image sensing apparatus 10 comprises a stimulating ray source 20 for producing stimulating rays L1, which have wavelengths falling within the stimulation wavelength range for the light-sensitive substance, and an image sensing means 21 for detecting the fluorescence L2, which is produced by the light-sensitive substance, and converting the fluorescent image of the sick portion 15 into an image signal S1. The image sensing means 21 may be constituted of a high-sensitivity CCD camera, or the like.

The image projecting apparatus 11 comprises an image reproducing means, which may be constituted of a liquid crystal display panel, or the like, and a projecting optical system for projecting the image, which has been reproduced and displayed on the image reproducing means, onto the sick portion 15 of the patient 14. An image sensing means 22, which may be constituted of a CCD camera, or the like, is secured to the image projecting apparatus 11. The image sensing means 22 constitutes an image position matching means in cooperation with the fluorescent markers 17, 17 for position matching and the control unit 13.

How this embodiment of the surgical operation aiding system in accordance with the present invention operates will be described hereinbelow. When a surgical operation is to be conducted in order to cut off a tumor from the sick portion 15, the stimulating ray source 20 of the fluorescent image sensing apparatus 10 is activated in order to produce the stimulating rays L1. The stimulating rays L1 are irradiated to the sick portion 15. As a result, the light-sensitive substance having been absorbed in the sick portion 15 is stimulated by the stimulating rays L1 and produces the fluorescence L2. The image sensing means 21 detects the fluorescence L2 and converts the fluorescent image of the sick portion 15 into the image signal S1. The image signal S1 representing the fluorescent image is fed into the control unit 13.

Figure 3A:
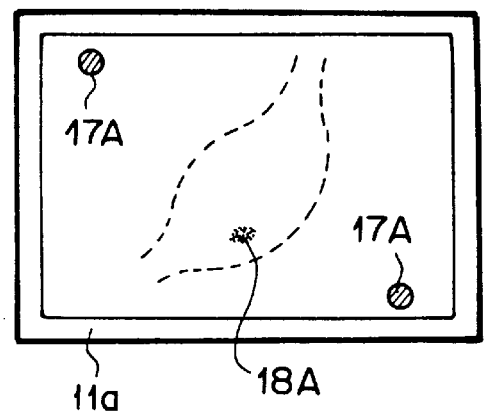
FIGS. 3A, 3B, and 3C are explanatory views showing how the image of a sick portion is displayed in the embodiment of the surgical operation aiding system in accordance with the present invention.

The control unit 13 carries out conversion processing for the position matching, which will be described below, on the image signal S1. An image signal S2 is obtained from the conversion processing. The image signal S2 is fed into the image projecting apparatus 11. The image reproducing means, such as the liquid crystal display panel, of the image projecting apparatus 11 reproduces the fluorescent image of the sick portion 15 from the image signal S2 and displays it. FIG. 3A schematically shows how the fluorescent image of the sick portion 15 is displayed on the image reproducing means 11a of the image projecting apparatus 11. As illustrated in FIG. 3A, the fluorescent image, in which a pattern 18A of the tumor located in the sick portion 15 is illustrated clearly, is displayed on the image reproducing means 11a. In FIG. 3A, reference numeral 17A represents the pattern of the marker. The image projecting apparatus 11 projects the displayed fluorescent image onto the actual sick portion 15 of the patient 14.

Figure 3B:
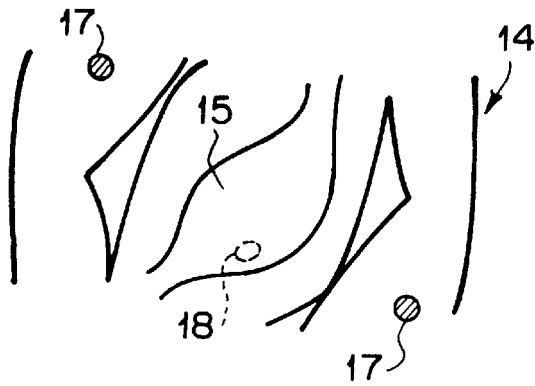
Figure 3C:
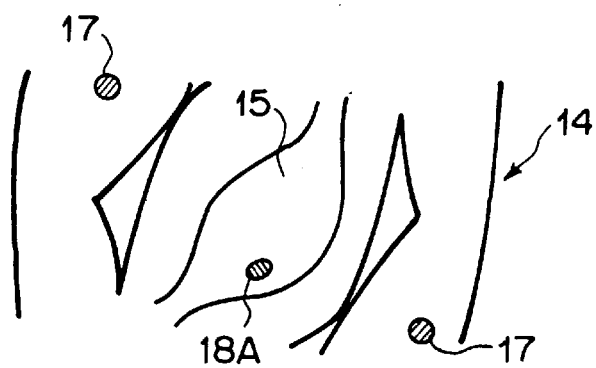

FIG. 3B is an explanatory view showing how the actual sick portion 15 of the patient 14 is seen by the unaided eyes. A tumor 18, the pattern 18A of which is illustrated in the fluorescent image, is located in the actual sick portion 15. Ordinarily, due to reasons, such as the dark state in the operating room, as described above, it often occurs that the tumor 18 cannot be clearly found by the unaided eyes. However, in the embodiment of the surgical operation aiding system in accordance with the present invention, the fluorescent image displayed on the image reproducing means 11a of the image projecting apparatus 11 is projected onto the actual sick portion 15 such that the position of the pattern of the sick portion, which is illustrated in the fluorescent image, and the position of the actual sick portion 15 may match with each other. Therefore, as illustrated in FIG. 3C, the tumor pattern 18A is projected to and displayed at the position on the actual sick portion 15, at which the tumor 18 is actually located.

Accordingly, the surgical operator can accurately determine the location and the size of the tumor 18 in the actual sick portion 15 by making reference to the tumor pattern 18A illustrated in the projected and displayed image. An accurate surgical operation can thus be conducted such that the cut-off range may be limited to the minimum necessary range.

How the matching of the position of the actual sick portion 15 and the position of the pattern of the sick portion illustrated in the fluorescent image is carried out will be described hereinbelow. The image sensing means 22, which is secured to the image projecting apparatus 11, detects the image of the actual sick portion 15 together with the patterns of the fluorescent markers 17, 17 for position matching. An image signal S3 representing the thus detected image for position matching is obtained from the image sensing means 22. The image signal S3 is fed into the control unit 13. The control unit 13 carries out the conversion processing for image size enlargement and reduction and image rotation on the image signal S1 such that the positions of the picture elements in the patterns of the fluorescent markers 17, 17 for position matching, which picture elements are represented by the image signal S3, and the positions of the picture elements in the patterns of the fluorescent markers 17, 17 for position matching, which picture elements are represented by the image signal S1 having been received from the fluorescent image sensing apparatus 10, may coincide with each other.

The position of the image projecting apparatus 11 and the position of the image sensing means 22 with respect to each other are set such that, when the positions of the picture elements in the patterns of the fluorescent markers 17, 17 for position matching, which picture elements are represented by the image signal S3, and the positions of the picture elements in the patterns of the fluorescent markers 17, 17 for position matching, which picture elements are represented by the image signal S1, coincide with each other, the position of the actual sick portion 15 and the position of the pattern of the sick portion in the projected image may match with each other. Accordingly, the fluorescent image is reproduced from the image signal S2, which has been obtained from the aforesaid conversion processing, and the reproduced image is projected onto the actual sick portion 15. As a result, the tumor pattern 18A is projected to and displayed at the position on the actual sick portion 15, at which the tumor 18 is located.

In the embodiment described above, the processing for image size enlargement and reduction (i.e., alteration of the magnification of the projected image) and image rotation (i.e., alteration of the orientation of the projected image) is carried out on the image signal S1. Alternatively, only either one of the processing for the image size enlargement and reduction and the processing for the image rotation may be carried out. For example, in cases where the direction of projection of the fluorescent image can be strictly set to be a predetermined direction, only the processing for the image size enlargement and reduction may be carried out.

In this embodiment, an MRI image signal S4 is obtained from the MRI apparatus 12. The MRI image signal S4 is also fed into the control unit 13. Therefore, in lieu of the fluorescent image described above, the MRI image of the sick portion 15, which image is represented by the MRI image signal S4, can be projected and displayed on the actual sick portion 15 of the patient 14. Accordingly, the surgical operator can also determine the position of the diseased part by making reference to the MRI image. In such cases, the matching of the position of the pattern of the sick portion in the displayed image and the position of the actual sick portion may be carried out in the same manner as that described above. As for an MRI image, in which the patterns of the fluorescent markers 17, 17 for position matching have not been recorded, the position matching may be carried out by using the conventional pattern matching technique, or the like.

In lieu of the aforesaid MRI apparatus 12 and the fluorescent image sensing apparatus 10, or in addition to them, a different apparatus, such as an X-ray CT scanner or an ultrasonic diagnostic apparatus, may be connected to the control unit 13. In this manner, an image represented by an image signal, which is obtained from such a different apparatus, may be projected onto the sick portion of the patient.

The fluorescent image sensing apparatus 10 and the image projecting apparatus 11 may be incorporated in an illuminating apparatus for surgical operations or a microscope apparatus for surgical operations. Also, in lieu of the image projecting apparatus 11, an apparatus for scanning a light beam on the sick portion and thereby displaying the image on the sick portion may be employed.

In the claims:

1. A surgical operation aiding system, comprising:

i) means for generating an image signal representing an image of an internal structure of a portion of a living body, ii) means for reproducing said image signal and for displaying a reproduced image directly onto said portion of the living body, and iii) means for adjusting at least one of the magnification and the orientation of said reproduced image such that the position of said reproduced image displayed on the living body coincides with the position of said portion of the living body.

2. A system as defined in claim 1, wherein said portion of the living body has absorbed a light-sensitive substance, which is capable of producing fluorescence upon stimulation, said means for generating said image signal being arranged to irradiate stimulating rays, having respective wavelengths falling within a stimulation wavelength range for said light-sensitive substance, to said portion of the living body, to detect a fluorescent image produced from said portion having absorbed said light-sensitive substance, and to convert said fluorescent image into said image signal.

3. A system as defined in claim 1, wherein said means for generating said image signal is a magnetic resonance imaging apparatus.

* * * * *